United States Patent [19]
Gibbs et al.

[11] Patent Number: 5,817,475
[45] Date of Patent: Oct. 6, 1998

[54] AUTOMATIC MICROBIOLOGICAL TESTING APPARATUS AND METHOD

[75] Inventors: David L. Gibbs, New York; Wei-Fang Hsia, Bayside; Qi Wang, New York, all of N.Y.

[73] Assignee: Giles Scientific, Inc., New York, N.Y.

[21] Appl. No.: 746,734

[22] Filed: Nov. 15, 1996

[51] Int. Cl.⁶ .................................................. C12Q 1/02
[52] U.S. Cl. .............................. 435/29; 435/4; 435/287.1
[58] Field of Search .............................. 435/4, 29, 287.1, 435/283.1

[56] References Cited

U.S. PATENT DOCUMENTS

| | | |
|---|---|---|
| 3,297,873 | 1/1967 | Hovnanian et al. . |
| 3,525,803 | 8/1970 | Smart ........................................... 178/6 |
| 3,953,355 | 4/1976 | Potter et al. . |
| 3,999,047 | 12/1976 | Green . |
| 4,038,151 | 7/1977 | Fadler et al. . |
| 4,048,616 | 9/1977 | Hart et al. . |
| 4,061,469 | 12/1977 | DuBose . |
| 4,166,095 | 8/1979 | Kling et al. . |
| 4,170,987 | 10/1979 | Anselmo et al. . |
| 4,175,860 | 11/1979 | Bacus . |
| 4,191,940 | 3/1980 | Polcyn et al. . |
| 4,193,694 | 3/1980 | Smith . |
| 4,252,897 | 2/1981 | Axford et al. . |
| 4,358,203 | 11/1982 | Citrin . |
| 4,367,043 | 1/1983 | Sweet et al. . |
| 4,400,353 | 8/1983 | Meserol et al. . |
| 4,453,220 | 6/1984 | Flegal et al. . |
| 4,454,939 | 6/1984 | Kampf et al. . |
| 4,580,895 | 4/1986 | Patel . |
| 4,634,576 | 1/1987 | Galle et al. . |
| 4,676,951 | 6/1987 | Armes et al. . |
| 4,678,894 | 7/1987 | Shafer . |
| 4,684,244 | 8/1987 | Butts et al. . |
| 4,720,463 | 1/1988 | Farber et al. . |
| 4,724,215 | 2/1988 | Farber et al. . |
| 4,856,073 | 8/1989 | Farber et al. . |
| 5,340,747 | 8/1994 | Eden . |
| 5,645,800 | 7/1997 | Masterson et al. ........................ 422/65 |

OTHER PUBLICATIONS

Arun N. Netravali, et al., "Digital pictures: representation, compression, and standards," *Applications of communications theory*, pp. 38–49 and 290–292, 1995.

Julius T. Tou, et al., "Pattern recognition principles," *Applied methematics and computation*, No. 7, pp. 94–101, 1974.

John R. Smith, et al., "Automated Image Retrieval Using Color and Texture," Columbia University, Dept. of Electrical Engineering and Center for Telecommunications Research, New York, pp. 1–56, 1996.

James D. Foley, et al., "Computer Graphics: principles and practice," *Addison–Wesley systems programming series*, pp. 590–595, 1990.

*Primary Examiner*—John Kight
*Assistant Examiner*—Dameron Jones
*Attorney, Agent, or Firm*—R. Neil Sudol; Henry D. Coleman

[57] ABSTRACT

A microbiological assay investigatory apparatus has a source of electromagnetic waveform energy, a support and a linear color sensor. The support serves to hold a microbiological assay tray in a predetermined location relative to the source and to the sensor. The assay tray has different reaction chemicals and microorganisms of the same type in respective wells or chambers. The linear color sensor is disposed in a predetermined position relative to the support and concomitantly the assay tray for receiving electromagnetic waveform radiation emanating from a linear array of the wells in response to waveform energy from the source. The linear color sensor generates a signal encoding colorimetric data pertaining to a series of samples lying along a line intersecting the linear array of the wells.

19 Claims, 4 Drawing Sheets

AUTOMATIC MICROBIOLOGICAL TESTING APPARATUS AND METHOD

BACKGROUND OF THE INVENTION

The present invention relates to a microbiological testing apparatus and an associated method. More specifically, the present invention relates to an apparatus and associated method for use in identification and antibiotic susceptibility testing of samples, such as those from patients possibly infected by a microorganism.

A substantial portion of microbiological sample testing currently performed relies on the visual inspection of assay wells to determine the possible presence of color changes indicating that particular chemical reactions have occurred. The chemical reactions indicate that microbial samples in the wells have consumed or produced certain chemical compounds giving rise to respective color changes in respective wells of the assay tray. This method is expensive and time consuming. Personnel must be trained to distinguish closely related colors. In addition, the visual monitoring of assay wells takes considerable time even for experienced personnel.

Many automated systems have been proposed and/or developed for reading results of microbiological test samples for providing information on the identification of the causative organism, and the susceptibility of that organism to various antimicrobial agents. It is desirable to use automated systems to read test results to minimize the subjective conclusions from technicians regarding color, color patterns, and or optical density in an assay well.

Several proposed or existing automated systems include moving of the assay trays and sensors relative to one another. Of course, such systems, with their motors and moving parts, require costly and complex servicing. Accordingly, it is not only desirable to arrive at test results very rapidly, but it is also advantageous to eliminate motors and minimize moving parts that require costly and complex servicing.

U.S. Pat. Nos. 4,720,463, 4,724,215, and 4,865,973 describe an apparatus and method that relies on a camera producing a two dimensional image or picture, which is then analyzed. That apparatus and method have not achieved a broad commercial success due to inherent difficulty in reading multiple tests at one time in elongated trays, due to distortion by the camera lens of objects at the edges, broad variation in colors and intensity across a broad range has tended to reduce the quality of image, and the quantity of data in two dimensional images entails a high degree of complexity in transmission and microprocessor analysis of that two dimensional data if it is to be utilized maximally.

U.S. Pat. No. 5,340,747 describes an apparatus and method that requires a narrow band light source and a narrow band filter which essentially eliminates the ability to detect and analyze a broad range of colors or color patterns.

U.S. Pat. No. 4,676,951 describes a complex highly mechanized apparatus that relies on a relatively commonly approach of optical diode light detectors. This approach has the disadvantage that high quality diodes are often costly. Moreover, to eliminate placement of multiple diodes, at least one per sample chamber, a tray of test chambers is generally moved by motors at a given rate under the light detector(s). This solution adds significant cost and servicing problems. Optical diodes have a very major limitation in this application in that they only record the average light collected at a single spot or area around a spot; they are unable to collect enough information in a given test chamber to distinguish color patterns that can greatly increase the accuracy of test result determinations.

OBJECTS OF THE INVENTION

An object of the present invention is to provide an improved apparatus and/or associated method for microbiological testing.

Another object of the present invention is to provide an essentially automated microbiological testing apparatus and/or method wherein color detecting and evaluation is performed automatically.

A further object of the present invention is to provide such an automated microbiological testing apparatus and/or method wherein motors and other moving parts are minimized, if not eliminated.

An additional object of the present invention is to provide such an automated microbiological testing apparatus and/or method wherein test results are determined based on as much informational experience as possible.

Yet another object of the present invention is to provide such an automated microbiological testing apparatus and/or method wherein the disadvantages of cameras, referred to above, are partially, if not completely, eliminated.

These and other objects of the present invention will be apparent from the descriptions and illustrations provided herein.

BRIEF DESCRIPTION

A microbiological assay investigatory apparatus comprises, in accordance with the present invention, a source of electromagnetic waveform energy, a support and a linear color sensor. The support serves to hold a microbiological assay tray in a predetermined location relative to the source and to the sensor. The assay tray has different reaction chemicals and microorganisms of the same type in respective wells or chambers. The linear color sensor is disposed in a predetermined position relative to the support and concomitantly the assay tray for receiving electromagnetic waveform radiation emanating from a linear array of the wells in response to waveform energy from the source. The linear color sensor generates a signal encoding colorimetric data pertaining to a series of samples lying along a line intersecting the linear array of the wells.

Preferably, there are two separate sources of electromagnetic waveform energy, one generating electromagnetic waveform energy in an ultraviolet frequency band and the other generating electromagnetic waveform energy in a visible frequency band. It is contemplated that the ultraviolet energy source is located above and lateral to the assay tray, while the visible-light source is disposed below the assay tray. A screen is insertable between the visible-light source and the sensor to selectively block light emitted by the visible-light source. This blocking facilitates detection by the sensor of low intensity radiation emanating from the wells in the linear array in response to the ultraviolet radiation.

A filter may be positioned between the ultraviolet energy source and the sensor for blocking UV radiation from reaching the sensor. This measure ensures that the sensor does not have a data distorting output owing to the effect of the ultraviolet light on the sensor components.

The signal from the sensor encoding the colorimetric data is an analog signal which is transformed to a binary or digital signal via an analog-to-digital converter. This digital colorimetric signal is then fed to a storage component or buffer register. The buffer register is connected to a computer or digital processor which performs a color analysis.

The colorimetric data from the linear color sensor is in the form of RGB (red, green, blue) magnitudes. The computer includes software-modified digital processing circuits for converting the RGB magnitudes to HSI (hue, saturation, intensity) values. In the memory of the computer or processor are stored previously determined data identifying, for each of the wells, a region in HSI space representing a positive chemical reaction result for the respective well. By "HSI space" is meant a collection of all possible HSI ordered triplets (all possible combinations of hue, saturation, and intensity). A region of positive test results in HSI space for a given assay well is a subset of HSI ordered triplets (hue, saturation and intensity values). If a particular test result, i.e., a particular combination of hue, saturation and intensity for a selected assay well, falls within the "positive" region for that well, then a chemical reaction has occurred in that well.

The computer or processor additionally includes software-modified digital processing circuits for determining whether an HSI value from a selected well falls within the respective "positive" region in HSI space. Generally, each selected well of the assay test tray carries a chemical solution of a certain color, which can be associated with a respective region in HSI space. Thus, if a particular HSI test result for that selected well falls within the respective beginning color region, where no reaction has occurred, then there is clearly a negative test result. If a particular HSI test result for the selected well falls outside both the negative and the positive regions in HSI space, then several different approaches are available for identifying the test result. One approach is to specify the test result as indeterminate (neither positive nor negative). Another approach is to designate all areas outside the particular positive and negative regions in HSI space as being negative test results. Yet another approach to is designate an unclear result as being positive if it is close enough to the positive region in HSI space. for example, if the unclear result is closer to the positive region than to the associated negative region. This determination can be implemented by two straightforward distance determinations and a comparison of the two calculated distances.

Where the assay tray contains chemical test wells disposed in a plurality of linear arrays (rows, columns), there is preferably provided a plurality of linear color sensors disposed in respective predetermined positions fixed relative to the tray support and concomitantly the assay tray for simultaneously receiving electromagnetic waveform radiation emanating from respective linear arrays of the wells and for generating respective signals encoding colorimetric data pertaining to respective series of samples lying along respective lines intersecting the respective linear arrays of the wells.

It is to be emphasized that the output from a sensor used in the present invention is a series of samples extending along a line.

Preferably, a lens is positioned between the support and the sensor for focusing light from the wells on the sensor. Thus, the sensor can have a length considerably shorter than the distance between the first and the last wells in the respective linear array of wells on the test tray. Also, a mask is advantageously disposed between the tray support and the sensor for reducing background light from reaching the sensor.

A microbiological assay investigatory method comprises, in accordance with the present invention, (i) generating electromagnetic waveform energy, (ii) holding a microbiological assay tray in a predetermined location relative to the source, the assay tray having different reaction chemicals and microorganisms of the same type in respective wells or chambers, and (iii) operating a linear color sensor to receive electromagnetic waveform radiation emanating from a linear array of the wells in response to waveform energy from the source and to generate a signal encoding colorimetric data pertaining to a series of samples lying along a line intersecting the linear array of the wells.

Pursuant to a feature of the present invention, the method further includes (iv) automatically converting the RGB magnitudes to HSI values, (v) storing previously determined data identifying, for each of the wells, a region in HSI space representing a positive chemical reaction result for the respective well, and (vi) analyzing an HSI value from a selected well in relation to the respective region in HSI space to determines whether the HSI value from the selected well falls within the respective region in HSI space.

The present invention greatly simplifies the mechanical design and reliability of software-implemented (automatic) test result analysis, by using a linear color sensor that is held in a fixed position relative to the sample test chambers to provide only one line of high quality color information. This simplified design reduces manufacturing and servicing costs and tends to increase reliability of the apparatus in commercial applications.

The present invention also enables positioning the linear sensor at a fixed distance from the object that allows the assay wells to be illuminated using deflected light from above and adjacent to the tray of wells, and/or using transmitted light from beneath the tray of wells, thus providing, with one fixed linear sensor array system, the ability to read a very broad range of light wavelengths, thus enabling a broader range of test samples to be read. The holder member is positioned at a height above the object such that the focusing lens captures light from wells and directs it into the linear color sensor. The linear color sensor assembly is a very simple device and usually contains a slit mask to block background light and thereby shine only a line of light on the sensor array. A broad band-pass-type light filter may also be positioned in front of the linear sensor to block broad regions of the light spectrum if they would tend to interfere with appropriate sample well color detection. A substantially automated apparatus and associated method for microbiological testing in accordance with the present invention has advantages of speed, accuracy, and reduced overall costs. In addition, because an apparatus in accordance with the present invention has essentially no moving parts, the apparatus does not require expensive maintenance and repair. The computer's memory can be easily updated to incorporate more precise definitions of "positive" test regions, thereby increasing accuracy of the apparatus and associated method with increasingly accumulated test data. Thus, test results are determined based on as much informational experience as possible.

In an apparatus and associated method for microbiological testing in accordance with the present invention, the disadvantages of cameras are partially, if not completely, eliminated.

DESCRIPTION OF THE PREFERRED EMBODIMENTS

Figure 1:
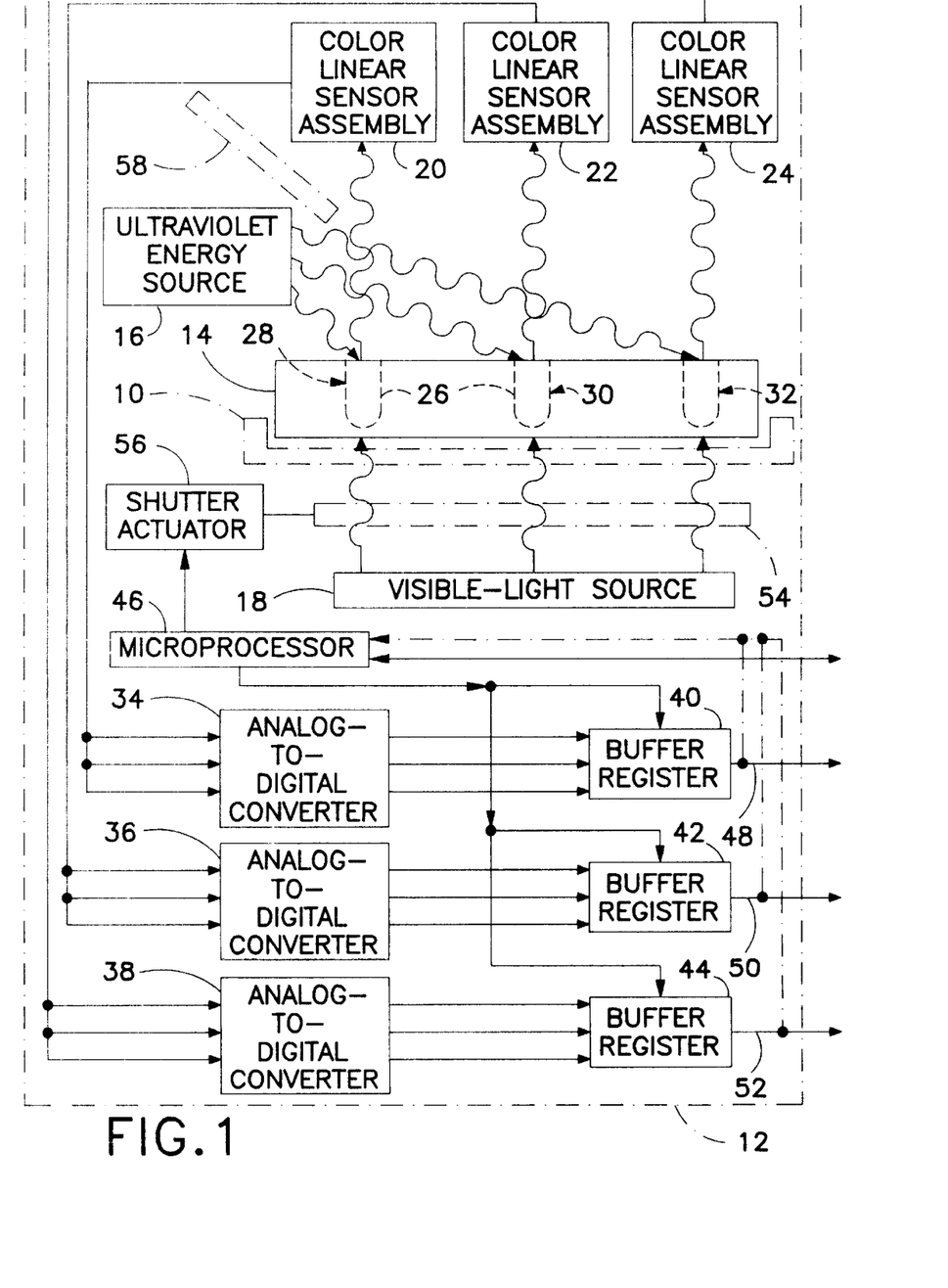
FIG. 1 is a block diagram of a microbiological testing apparatus in accordance with the present invention.

As illustrated in FIG. 1, an automated microbiological testing apparatus comprises a support element 10 attached to a frame or housing 12 for holding a microbiological assay tray 14 in a predetermined location fixed relative to a source 18 of visible light (electromagnetic waveform energy), a source 16 of ultraviolet electromagnetic waveform energy and a plurality of linear color sensor assemblies 20, 22, and 24. Sources 16 and 18, as well as assemblies 20, 22, and 24, are mounted to frame or housing 12.

Assay tray 14 is a commercially available product which has a plurality of wells or chambers 26 which carry different reaction chemicals and microorganisms of the same type. The microorganism is obtained from a patient, in which case the assay tray is used to identify the microorganism. Alternatively, a known microorganism is being tested for its susceptibility to different drugs.

Linear color sensor assemblies 20, 22, and 24 receive electromagnetic waveform radiation which is emitted from wells in respective linear arrays 28, 30 and 32 in response to ultraviolet waveform energy from source 16 or visible waveform energy from source 18. In response to incoming light energy, linear color sensor assemblies 20, 22 and 24 generate respective RGB (red, green, blue) signals encoding colorimetric data which pertain to respective series of samples lying along lines intersecting the wells of respective linear arrays 28, 30, and 32. Accordingly, each set of red, green and blue magnitudes or intensities encoded in analog voltages from linear color sensor assemblies 20, 22, and 24 corresponds to a single sample along a line extending through the wells of a linear well array 28, 30, and 32.

Linear color sensor assemblies 20, 22, and 24 are operatively connected at respective outputs to respective analog-to-digital converters 34, 36, and 38 which transform the analog RGB magnitudes to digitally encoded values. These digital RGB values are temporarily stored in buffer registers 40, 42, and 44 prior to transmission to a general purpose computer (not shown) or a microprocessor 46 attached to frame or housing 12. Each analog-to-digital converter block 34, 36, and 38 shown in FIG. 1 generally comprises three converter units dedicated to the red, green, and blue signals, respectively. Likewise, buffer registers 40, 42, and 44 each include three register units and have three-lead output multiples 48, 50, and 52, respectively.

Because light energy emanating from wells 26 in response to visible light energy from source 18 is so much more intense than the light emitted by the wells in response to ultraviolet radiation from source 16, a shutter 54 is provided to selectively block light from source 18 from reaching wells 26. Shutter 54 is operated by an actuator 56 under the control of local microprocessor 46. Microprocessor 46 is connected to buffer registers 40, 42, and 44 for coordinating the storage operations thereof with the actuation of shutter 54 so that for each assay tray 14 disposed on support 10, each well has two sets of RGB values, one generated in response to the irradiation of wells 26 by visible light from source 18 and the other generated in response to the irradiation of wells 26 by ultraviolet energy from source 16.

Figures 2, 4, 5:
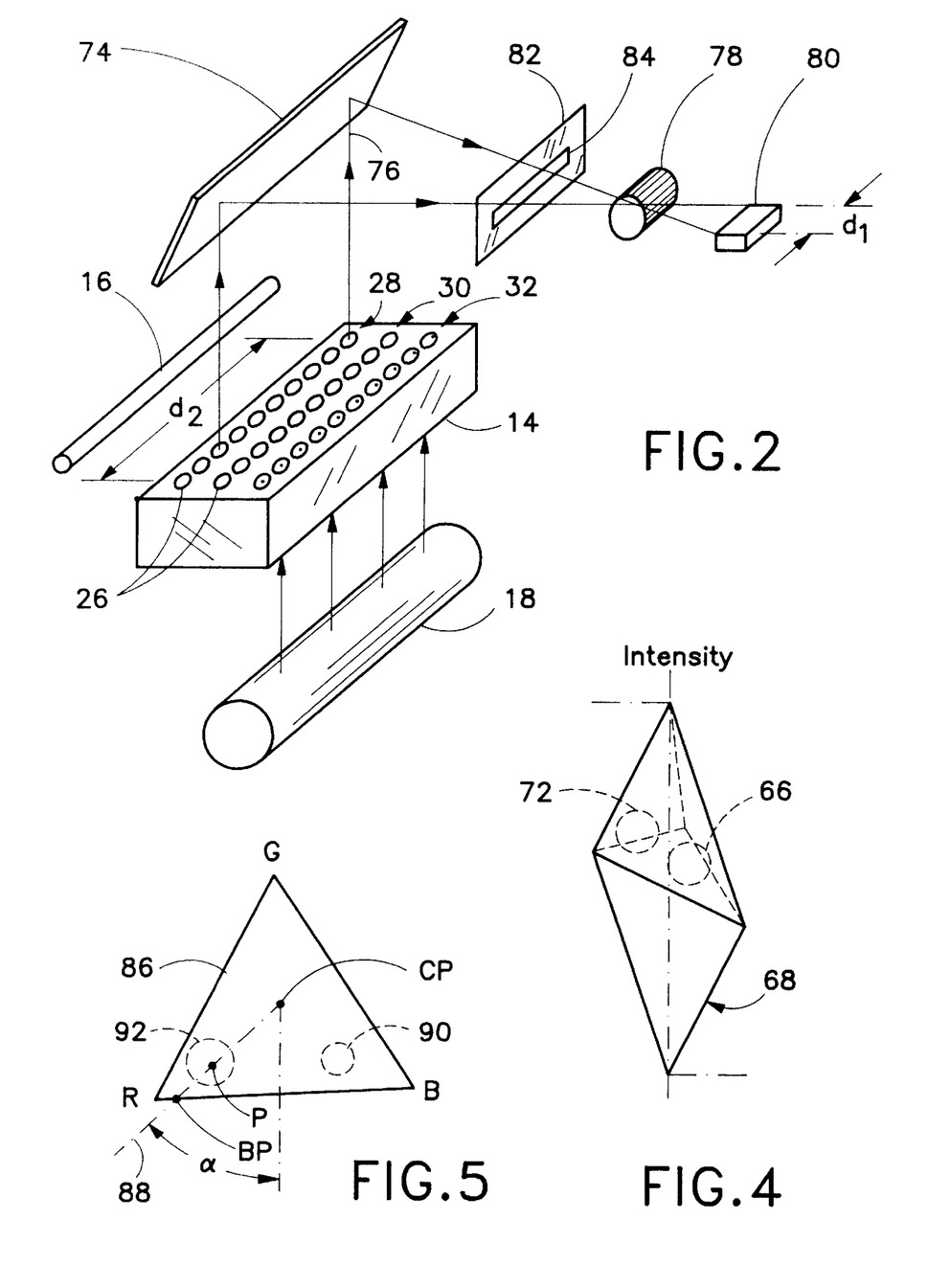
FIG. 2 is an isometric diagram, showing essential components of an embodiment of the present invention.
FIG. 4 is a diagram of HSI (hue, saturation, intensity) space with schematically indicated regions in that space representing positive and negative chemical reaction results for a selected well of an assay tray illustrated in FIGS. 1 and 2.
FIG. 5 is a diagram representing a constant intensity (I) plane through the HSI space illustrated in FIG. 3.

As indicated in FIGS. 1 and 2, it is contemplated that ultraviolet energy source 16 is located above and lateral to assay tray 14, while visible-light source 16 is disposed below assay tray 14. However, other relative positions are possible. A screen 58 is provided between ultraviolet energy source 16 and sensor assemblies 20, 22, and 24 for blocking UV radiation from reaching the sensors. This measure ensures that sensor assemblies 20, 22, and 24 do not have a data distorting output owing to the effect of the ultraviolet light on the sensor components.

Figure 3:
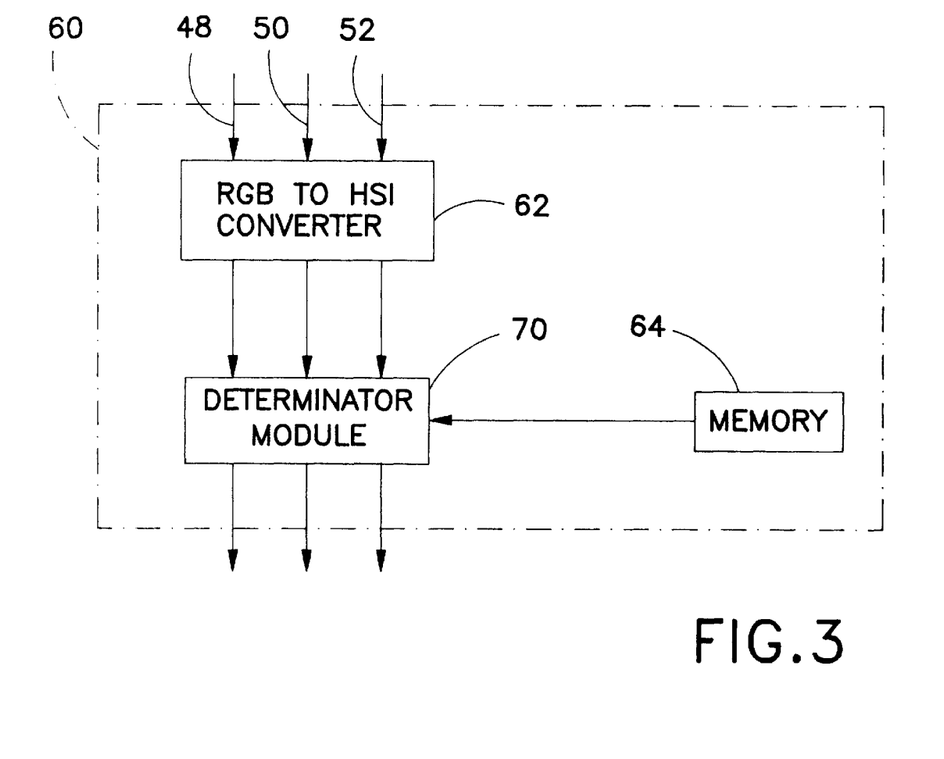
FIG. 3 is a block diagram of software-implemented computer modules in a computer or processor connected to the apparatus of FIG. 1 or included in the apparatus of FIG. 1.

The RGB data in registers 40, 42, and 44 is converted into ordered triplets in HSI (hue, saturation, intensity) space, that is, each set of red, green, and blue intensity values is transformed into a corresponding set of hue, saturation, and intensity values, by and external computer 60. As illustrated in FIG. 3, computer 60 (or microprocessor 46) includes a software-modified digital processing circuit or module 62 for converting the RGB magnitudes to HSI (hue, saturation, intensity) values. A memory 64 of computer 60 or processor 46 stores previously determined colorimetric reference data.

The colorimetric reference data in memory 64 identifies, for each well 26 of each assay tray 14, a region 66 (FIG. 4) in HSI space 68 (FIG. 4) representing a positive chemical reaction result for the respective well 26. By "HSI space" 68 is meant a collection of all possible HSI ordered triplets (all possible combinations of hue, saturation, and intensity). Region 66 of positive test results in HSI space 68 for a given assay well is a subset of HSI ordered triplets (hue, saturation and intensity values). If a particular test result, i.e., a particular combination of hue, saturation and intensity for a selected assay well, falls within the "positive" region 66 for that well, then a chemical reaction has occurred in that well.

It is to be noted that the graphic representation of HSI space 68 shown in FIG. 4 is one of several possible graphic representations. For mathematical purposes, it is easier to work with HSI space if the space is represented in cylindrical coordinates. In that case, the intensity dimension lies along the axis of a cylinder, while the hue dimension is an angle about the axis and the saturation is a distance along a radius line. A more accurate representation of HSI space may be a pair of cones tapering down in opposite directions away from a common plane. The intensity dimension lies along a common axis of two cones, while the hue value of a point in the HSI space corresponds to an angle about the axis of a radius line to the point and the saturation is a proportion of (1) the distance to the point along that radius line to (2) the distance to an outer surface of the space along that radius line (i.e., the radius of the circular section in a plane transverse to the common axis).

Computer 60 or processor 46 additionally includes a software-modified digital processing circuit or module 70 for determining whether an HSI value from a selected well falls within the respective "positive" region in HSI space.

Generally, each selected well 26 (FIG. 1) of an assay test tray 14 carries a chemical solution of a certain color, which can be associated with a respective "negative" region 72 in HSI space 68 (FIG. 4). Thus, if a particular HSI test result for that selected well falls within the respective beginning color region 72, then there is clearly a negative test result (no reaction). If a particular HSI test result for the selected well falls outside both the negative region 72 and the positive region 66 in HSI space 68, then several different approaches are available for identifying the test result. One approach is to specify the test result as indeterminate or undecided (neither positive nor negative). Another approach is to designate all areas outside the particular positive and negative regions in HSI space as being negative test results. Yet another approach to is designate an unclear result as being positive if it is close enough to the positive region in HSI space, for example, if the unclear result is closer to the positive region than to the associated negative region. This determination can be implemented by two straightforward distance determinations and a comparison of the two calculated distances. The distance calculation and the comparison may be executed by circuit or module 70 during the taking of test results. Alternatively, the distance determinations and comparisons may be performed beforehand, prior to the collection of test data. This prior determination results in a table, stored in member 64 of computer 60 or microprocessor 46, whereby each triplet in HSI space for each well is assigned a positive or negative value. Then, when HSI test data arrives via module 62, circuit or module 70 need only consult the table in memory 64 to ascertain whether a positive test result has occurred.

FIG. 2 shows a specific embodiment of the microbiological testing apparatus of FIG. 1, with only one sensor assembly 20 being depicted for purposes of simplicity. A mirror 74 is disposed along a light ray path 76 extending from wells 26 in linear array 28 of tray 14. Assembly 20 (as well as assemblies 22 and 24) includes a lens 78 positioned between support 10 and a linear color sensor chip 80 for focusing light from wells 26 of array 28 onto sensor chip 80. Thus, sensor chip 80 can have a length d1 considerably shorter than the distance d2 between the first and the last wells in array 28. A mask 82 with a slit 84 is advantageously disposed between tray support 10 and sensor chip 80 for reducing background light from reaching sensor chip 80.

FIG. 5 shows a triangular locus or subset 86 of HSI triplets having a single intensity value in HSI space. A point P represents a particular HSI triplet having that single intensity value. A center point CP represents an HSI triplet which has no saturation value and no hue and thus corresponds to a gray tone. A line 88 through points P and CP makes an angle α in plane 86 about point CP. That angle a corresponds to the hue value of point P. The proportion of (1) the distance of point P from center point CP to (2) the distance between the center point CP and a boundary point BP along the same radial line represents the saturation value of point P. Circles 90 and 92 represent the intersections of regions 66 and 68 with plane 86. Corners of locus or subset 86 represent pure red, green and blue (R, G, B) hues.

Figure 6:
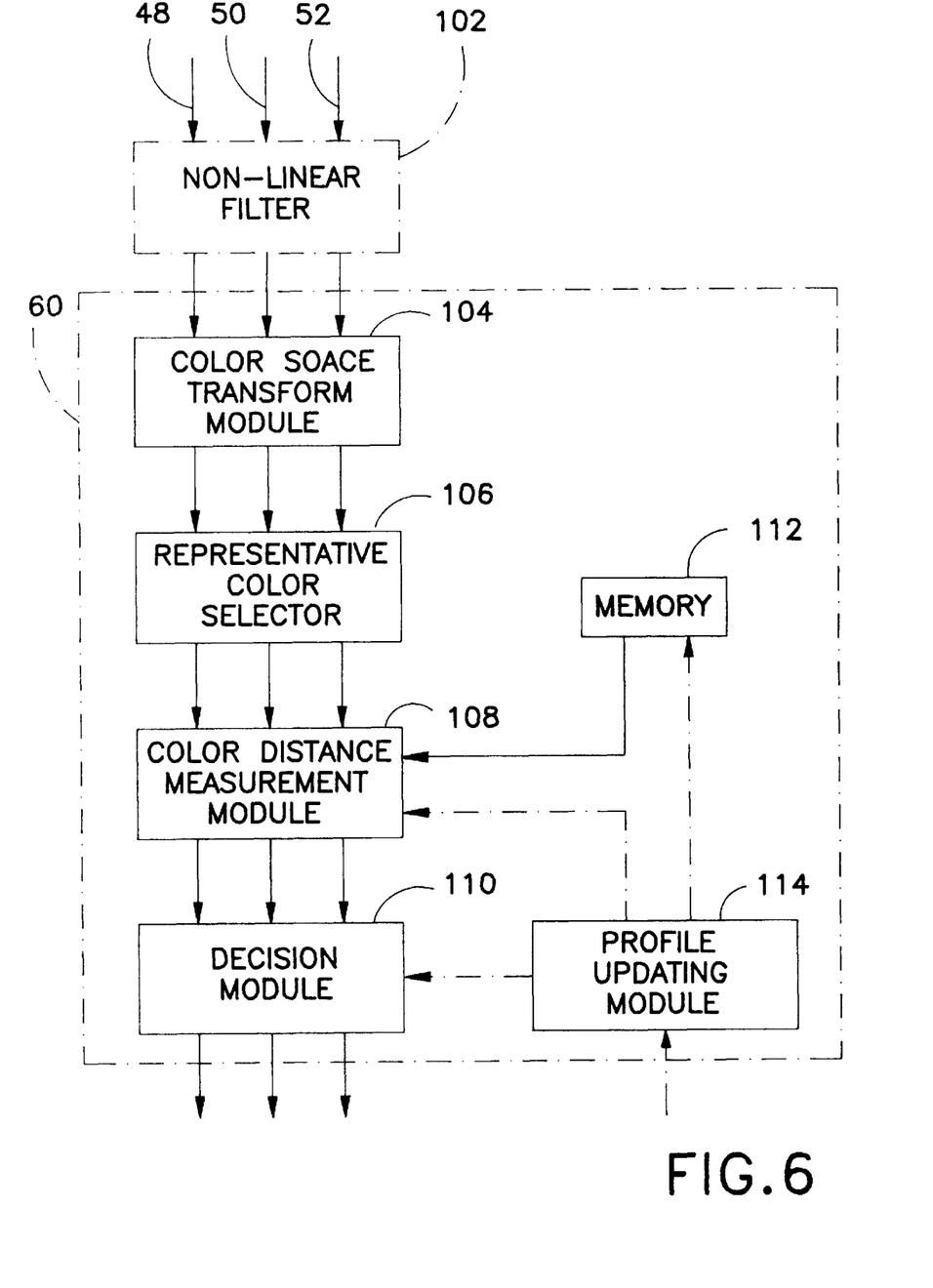
FIG. 6 is a functional block diagram similar to, but more detailed than, FIG. 3.

FIG. 6 is a functional block diagram similar to, but more detailed than, FIG. 3. The RGB color signals carried on multiples 48, 50, and 52 may be fed to an optional non-linear filter 102 for eliminating noise patterns generated in the scanning process. Filter 102 operates on all three color channels for each sensor assembly 20, 22, and 24 (FIG. 1). Color median filtering of radius 2 achieves good results.

As further illustrated in FIG. 6, the filtered RGB signals are fed to a color space transform module 104 which is identical to converter 62 in FIG. 3. The color space transform is a key step to be performed by computer 60 or microprocessor 46. RGB is the most commonly used color sample space. However, RGB space is not perceptually uniform. This means that distance functions defined in RGB space will not be satisfactory because perceptual distance is a function of position in RGB space. Other color spaces such as HSI (also known as HSV), LAB, LUV and Munsell offer improved perceptual uniformity. It is also easier to compensate for many artifacts and color distortions in color spaces other than RGB.

An algorithm executed by converter 62 (FIG. 3) or transform module 104 (FIG. 6) for implementing a conversion of RGB values to HSI values may proceed as follows. Let ordered triplet (r, g, b) represent a color point in RGB space and let ordered triplet (h, s, i) represent be the corresponding or transformed color point in HSI space. From a triplet or point (r, g, b) defined such that (r, g, b)∈0~1, the corresponding triplet or point (h, s, i) can be obtained as follows, where h∈0~6, s∈0~1, and i ∈0~1 (see *Measuring Color*, Hunt, R. W. G., John Wiley & Sons, 1989):

i = MAX (r, g, b)
Let mmm = i − MIN (r, g, b); then s = mmm/i.
Let r1 = (i − r)/mmm, g1 = (i − g)/mmm, b1 = (i − b)/mmm,
then if r = Max and g = Min then h = 5 + b1,
else if r = Max and g ≠ Min then h = 1 − g1,
else if g = Max and b = Min then h = 1 + r1,
else if g = Max and b ≠ Min then h = 3 − b1,
else if b = Max and r = Min then h = 3 + g1,
else h = 5 − r1.

In general, r, g, and b samples in real images are all quantized into 0~255, while h, s, and i samples are quantized into 0~360, 0~100, and 0~100, respectively.

Functions performed by determinator module 70 in FIG. 3 are performed by three software-determined digital processing circuits 106, 108, and 110. Circuit 106 is a representative color selector which mathematically combines a plurality of HSI values from a sequence of HSI values coming from the same well 26 in tray 14. Selector 106 calculates a representative value HSI value as a first order statistical value such as a mean or median. The median is preferred since it guarantees the existence of the representative color in the sample region.

The representative color sample in HSI space is transmitted from selector module 106 to software-determined digital processing circuit 108 which is a color distance measurement module. Basically, circuit or module 108 compares each incoming representative HSI sample with color samples in a color template profile (regions 66, 72 in FIG. 4) in a computer memory 112, with the comparison criterion being a distance measure. The most commonly used distance measure is Euclidean distance which represents the actual distance between two points in a three-dimensional color space.

The color distance measurement or calculation is implemented as follows. Let p(h, s, i) and q(h, s, i) represent two color points or triplets in HSI space. Then the Euclidean distance d between the color points or triplets p and q is defined as:

$$d^2(p, q) = \sum_{j=h,s,i} (p_j - q_j)^2$$

Various combinations of HSI channels may be used for distance measurement based on the training samples, to eliminate any uncorrelated channels in distance computation.

It is to be noted that each region 66 and 72 in HSI space may be reduced to a single point, assuming that the various regions 66 and 72 are spheres of a common radius. In that case, for each incoming HSI sample, module 108 makes two distance computations. The results of the distance computations are delivered to software-determined digital processing circuit 110 which implements a colorimetric decision for each well 26 in an assay tray 14 in response to the distance measurements made by module 108. Module 110 subtracts one distance value from the other to derive a difference value. Module 110 also averages the distance values. If the ratio of the distance difference to the distance average is less than a predetermined fraction (e.g., 0.1), then the respective incoming HSI sample is taken to have the result of the closer region (66 or 72). If the ratio of the distance difference to the distance average is greater than the predetermined fraction (0.1), then the respective incoming HSI sample is taken to have an undecided or indeterminate value.

Positive-result and negative-result regions 66 and 72 of HSI space are formed empirically and can be refined by an iterative process discussed in greater detail below. As a general matter, the more reference samples which have been collected to define positive-result and negative-result regions 66 and 72, the more accurate the definitions of the regions, whether those regions are defined by surfaces in HSI space or merely by a single ordered (h, s, i) triplet representing the center of a sphere having a common radius or by some other criteria. If the positive-result and negative-result regions 66 and 72 in HSI space are different from one another (have different radii or different shapes), the distance measurement or calculation implemented by module 108 may be weighted by a value obtainable during a representative color selection step in the calibration of the device.

As illustrated in FIG. 6, computer 60 or microprocessor 46 may include a module 114 for updating the color template profile, for example, to account for shifts in color sample distributions over time. Module 114 leads to the improvement of colorimetric test results over the long term. Module 114 enables the operator to selectively rewrite the contents of memory 112, to change the distance algorithm followed by module 108, and to alter the decision criteria followed by module 110. For example, instead of dividing HSI space into roughly equal positive-result and negative result zones separated by a generally plate-shaped subset of undecided or indeterminate HSI points, as discussed above with reference to FIG. 6, decision module 110 might compare (a) the computed distance of an HSI sample point from the center of the positive-result region and (b) the radius of the positive-result region to determine whether the sample point falls within that (spherical) region. If so, the HSI sample represents a positive test result. If not, the HSI sample represents a negative test result, as discussed above with reference to FIG. 4.

A training program for refining the definitions of positive-result and negative-result regions 66 and 72 of HSI space for the different wells 26 of a type of an assay tray 14 comprises an iterative or recursive process wherein an initial color template profile is obtained from representative colors (mean HSI values) of one or more groups of color evaluating personnel. This initial color template profile is used to evaluate a large number of samples including those known results using algorithms set forth above, thereby obtaining a new classification or result group. Representative colors (means) are computed for these result groups, the representative colors being used to form a new color template profile. This procedure is repeated, utilizing a K-mean methodology, until the result group is stable, i.e., until there are no differences between the previous result group and the new result group.

In defining positive- and negative-result regions 66 and 72, statistical tools may be used to eliminate bad samples. For example, for any given iteration of the recursive region refinement procedure, the boundaries of the regions may be defined as encompassing 98% of all samples. The extents of the positive-and negative-result regions 66 and 72 may then be expanded by a "lose factor" (e.g., 10%) to better define the statistically derived boundaries. The bad-sample elimination percentage, as well as the "lose factor," can be allotted different magnitudes depending on further empirical evaluation.

In some cases, one or two of the color channels or dimensions of the three dimensional HSI space may be superfluous to the evaluation of microbiological test results. For example, satisfactory results can be obtained in HSI space even if the intensity dimension is ignored or eliminated. In this case, the distance computation can be limited to two dimensions. In general, whether one or two color channels or dimensions may be omitted or eliminated in the evaluation of the colorimetric test data can be determined experimentally for the different commercial brands of microbiological assay trays.

It is to be noted that sensor chips 80 (FIG. 2) are disposed in respective fixed positions relative to test tray 14 during reading of test results. The fact that the linear array color sensor chips 80 are substantially fixed relative to each linear array 28, 30, 32 of wells 26 during the reading process eliminates the need to move an optical detector device from well to well, or move the tray of test wells under the optical detector, as is common with the optical diode approach. Movement of the test sample tray or the optical detector device is critical with the optical image scanner approach to produce a two dimensional image. The approach of using a video camera also produces a two dimensional image of the tray with the camera device being stationary during reading of the tests. The camera and scanner image analysis approach, however, result in an exponential increase in the data generated compared to the one dimensional linear color analysis approach described herein. Image processing increases greatly the complexity of analysis, especially in microbiological assays where color matching and only very basic patterns are of interest. Camera images often also produce difficulties in reading the test chambers on the edges of larger objects due to optical distortion by the lens at the edges of picture, or loss of resolution if the image size is reduced.

The microbiological test evaluation apparatus described herein is specifically useful in detecting a very broad range of colors and color patterns from a plurality of microbiological reaction chambers.

The present invention greatly simplifies the mechanical design relative to existing apparatus and results in better quality of data relative to both camera and scanner two dimensional images and single spot diode analysis. This simplified design reduces manufacturing and servicing cost, and tends to increase reliability of the apparatus in a commercial application.

Although the invention has been described in terms of particular embodiments and applications, one of ordinary skill in the art, in light of this teaching, can generate additional embodiments and modifications without departing from the spirit of or exceeding the scope of the claimed invention. For example, although HSI (HSV) space is disclosed above for the determination of colorimetric test results, other color spaces or coordinates systems could be used, such as LAB, LUV, or Munsell. Of course, although positive- and negative-result regions 66 and 72 are particularly described as being spherical, other shapes for those regions are possible, depending on the empirical data used to define the regions. Regions 66 and 72 may be ellipsoidal or kidney-shaped, as examples. Accordingly, it is to be understood that the drawings and descriptions herein are offered by way of example to facilitate comprehension of the invention and should not be construed to limit the scope thereof.

What is claimed is:

1. A microbiological assay investigatory apparatus comprising:

a source of electromagnetic waveform energy;

a support for holding a microbiological assay tray in a location relative to said source, said assay tray having different reaction chemicals and organism components of the same type in respective wells or chambers;

a linear light sensor fixed in a predetermined position relative to said support and concomitantly said assay tray for receiving electromagnetic waveform radiation emanating from a linear array of said wells in response to waveform energy from said source during a scanning or reading of said wells and for generating a signal encoding colorimetric data pertaining to a series of samples lying along a line intersecting said linear array of said wells; and a computer or digital-processor connected to said sensor and programmed to analyze said colorimetric data to determine the existence of possible color changes in aid wells resulting from chemical reactions induced by said organism components.

2. The apparatus defined in claim 1 wherein said source is one of a first source and a second source, said first source generating electromagnetic waveform energy in an ultraviolet frequency band and said second source generating electromagnetic waveform energy in a visible frequency band.

3. The apparatus defined in claim 2, further comprising a screen insertable between said second source and said sensor to selectively block light from said second source, thereby facilitating detection by said sensor of low intensity radiation emanating from said wells in said linear array in response to waveform energy from said first source.

4. The apparatus defined in claim 2, further comprising a filter positioned between said first source and said sensor for blocking UV radiation from reaching said sensor.

5. The apparatus defined in claim 2, wherein said first source is positioned above said support and concomitantly said assay tray in a location laterally displaced from said support.

6. The apparatus defined in claim 1, further comprising storage means connected to said sensor for temporarily storing colorimetric data and transmitting said colorimetric data to a computer or digital processor for analysis.

7. The apparatus defined in claim 1 wherein said linear light sensor is one of a plurality of separate linear light sensor units disposed in respective positions fixed relative to said support and concomitantly said assay tray for simultaneously receiving electromagnetic waveform radiation emanating from respective linear arrays of said wells and for generating respective signals encoding colorimetric data pertaining to respective series of samples lying, along respective lines intersecting the respective linear arrays of said wells.

8. The apparatus defined in claim 1, further comprising a lens positioned between said support and said sensor for focusing light from said wells on said sensor, also comprising a mask disposed between said support and said sensor for reducing background light from reaching said sensor.

9. The apparatus defined in claim 1 wherein said colorimetric data is in the form of RGB magnitudes, said computer including first software-modified digital processing circuits for converting said RGB magnitudes to HSI values, said computer or processor further including a store of previously determined data identifying, for each of said wells, a region in HSI space representing a positive chemical reaction result for the respective well, said computer or processor additionally including second software-modified digital processing circuits for determining whether an HSI value from a selected well falls within the respective region in HSI space.

10. A microbiological assay investigatory method comprising:

generating electromagnetic waveform energy;

holding a microbiological assay tray in a location relative to said source, said assay tray having different reaction chemicals organism components of the same type in respective wells or chambers;

operating a linear light sensor to receive electromagnetic waveform radiation emanating from a linear array of said wells in response to waveform energy from said source and to generate a signal encoding colorimetric data pertaining to a series of samples lying along a line intersecting said linear array of said wells; and operating a computer or digital processor, connected to said sensor, to analyze said colorimetric data to determine the existence of possible color changes in said wells resulting from chemical reactions induced by said organism components.

11. The method defined in claim 10 wherein the generating of waveform energy includes producing electromagnetic waveform energy in an ultraviolet frequency band and in a visible frequency band.

12. The method defined in claim 11, further comprising the step of selectively preventing irradiation of said wells by electromagnetic waveform energy in said visible frequency band, thereby facilitating detection by said sensor of low intensity radiation emanating from said wells in said linear array in response to waveform energy in said ultraviolet frequency band.

13. The method defined in claim 11, further comprising using a filter to block UV radiation from reaching said sensor.

14. The method defined in claim 11, wherein the electromagnetic waveform energy in said ultraviolet frequency band is emitted from a location above and laterally displaced from said assay tray.

15. The method defined in claim 10 wherein said linear light sensor is one of a plurality of linear light sensors disposed in respective positions fixed relative to said assay tray, further comprising operating said sensors to simultaneously receive electromagnetic waveform radiation emanating from respective linear arrays of said wells and to generate respective signals encoding colorimetric data pertaining to respective series of samples lying along respective lines intersecting the respective linear arrays of said wells.

16. The method defined in claim 10, further comprising focusing light from said wells on said sensor, also comprising reducing background light from reaching said sensor.

17. The method defined in claim 10 wherein said colorimetric data is in the form of RGB magnitudes, also comprising:

automatically converting said RGB magnitudes to color point values in a color space;

storing previously determined data identifying, for each of said wells, a region in said color space representing a positive chemical reaction result for the respective well; and analyzing a color point value from a selected well in relation to the respective region in said color space to determine whether the color point value from the selected well falls within the respective region in said color space.

18. The method defined in claim 17 wherein said analyzing of the color point value from the selected well includes computing a distance in said color space between the color point value from the selected well and the respective region.

19. A microbiological assay investigatory method comprising:

generating electromagnetic waveform energy;

holding a microbiological assay tray in a location relative to said source, said assay tray having different reaction chemicals and organism components of the same type in respective wells or chambers;

operating a color sensor to receive electromagnetic waveform radiation emanating from said wells in response to waveform energy from said source and to generate a signal encoding RGB colorimetric data pertaining to chemical reactions in respective ones of said wells;

automatically converting said RGB magnitudes to color point values in a color space;

storing previously determined data identifying, for each of said wells, a region in said color space representing a positive chemical reaction result for the respective well; and analyzing a color point value from a selected well in relation to the respective region in said color space to determine whether the color point value from the selected well falls within the respective region in said color space.

* * * * *